United States Patent
Masere et al.

(10) Patent No.: US 11,866,631 B2
(45) Date of Patent: *Jan. 9, 2024

(54) OXYGENATED AMINOPHENOL COMPOUNDS AND METHODS FOR PREVENTING MONOMER POLYMERIZATION

(71) Applicant: Ecolab USA Inc., St. Paul, MN (US)

(72) Inventors: Jonathan Masere, Richmond, TX (US); Ashish Dhawan, Aurora, IL (US)

(73) Assignee: Ecolab USA Inc., St. Paul, MN (US)

( * ) Notice: Subject to any disclaimer, the term of this patent is extended or adjusted under 35 U.S.C. 154(b) by 115 days.

This patent is subject to a terminal disclaimer.

(21) Appl. No.: 16/860,954

(22) Filed: Apr. 28, 2020

(65) Prior Publication Data

US 2020/0339880 A1 Oct. 29, 2020

Related U.S. Application Data

(60) Provisional application No. 62/840,109, filed on Apr. 29, 2019.

(51) Int. Cl.
| | | |
|---|---|---|
| *C09K 15/18* | (2006.01) | |
| *C09K 15/24* | (2006.01) | |
| *C08F 2/40* | (2006.01) | |
| *C07C 7/20* | (2006.01) | |
| *C07C 215/76* | (2006.01) | |

(52) U.S. Cl.
CPC ............... *C09K 15/24* (2013.01); *C07C 7/20* (2013.01); *C07C 215/76* (2013.01); *C08F 2/40* (2013.01); *C07C 2601/16* (2017.05)

(58) Field of Classification Search
CPC ........ C09K 15/04; C09K 15/20; C09K 15/24; C08F 2/40; C08F 2/42; C07C 7/20; C07C 17/42; C07C 63/04; C07C 215/74; C07C 215/76; C07C 215/78; C07C 215/84; C07C 215/86; C07C 215/88; C07C 217/78; C07C 217/80; C07C 217/82; C07C 217/84; C07C 217/88; C07C 217/90; C07C 217/92; C07C 217/94; C07C 2601/16
USPC ....... 252/182.29, 401, 403, 404, 405; 203/8, 203/9; 585/2, 3, 4, 5
See application file for complete search history.

(56) References Cited

U.S. PATENT DOCUMENTS

| | | | |
|---|---|---|---|
| 2,518,577 A * | 8/1950 | Thompson | C11B 5/0035 554/7 |
| 2,797,152 A * | 6/1957 | Hughes | C10L 1/2235 252/392 |
| 2,861,998 A * | 11/1958 | Reynolds | C08F 2/38 546/180 |
| 2,864,797 A | 12/1958 | De Groote et al. | |
| 2,907,801 A * | 10/1959 | Robert | C07C 7/20 585/860 |
| 3,010,912 A | 11/1961 | Hardman | |
| 3,432,401 A | 3/1969 | Tcherkawsky et al. | |
| 3,678,113 A | 7/1972 | Klopfer | |
| 3,696,050 A * | 10/1972 | Werts, III | C08K 5/18 523/508 |
| 3,697,275 A | 10/1972 | Hayakawa et al. | |
| 3,959,358 A | 5/1976 | Jursich | |
| 3,992,307 A | 11/1976 | Hotten | |
| 4,003,800 A | 1/1977 | Bacha et al. | |
| 4,021,310 A | 5/1977 | Shimizu et al. | |
| 4,038,434 A | 7/1977 | Young | |
| 4,117,238 A | 9/1978 | Ackermann et al. | |
| 4,337,103 A | 6/1982 | Elrick et al. | |
| 4,374,742 A | 2/1983 | Evans et al. | |
| 4,585,796 A | 4/1986 | Alig et al. | |
| 4,654,451 A * | 3/1987 | Miller | C07C 7/20 585/866 |
| 4,675,444 A | 6/1987 | Matsunaga et al. | |
| 4,692,544 A | 9/1987 | Goerner et al. | |
| 4,744,881 A | 5/1988 | Reid | |
| 5,103,032 A | 4/1992 | Turner et al. | |
| 5,213,699 A | 5/1993 | Babiarz et al. | |
| 5,219,480 A | 6/1993 | Gutierrez et al. | |
| 5,266,442 A | 11/1993 | Ooms | |
| 5,320,765 A | 6/1994 | Fetterman, Jr. et al. | |
| 5,340,369 A | 8/1994 | Koch et al. | |
| 5,443,596 A | 8/1995 | Junino et al. | |

(Continued)

FOREIGN PATENT DOCUMENTS

| | | | |
|---|---|---|---|
| CA | 467388 A * | 8/1950 | |
| CA | 467388 A | 8/1950 | |

(Continued)

OTHER PUBLICATIONS

Kluchesky et al. (1949) "Polymerization Inhibition and Stopping Agents", Ind. Eng. Chem., 41:1768-1771.
Voronkov et al. (1978) "XRN=2846043" Journal of General Chemistry of the USSR, vol. 48, 2 pages, abstract.
Ladona et al. (1999) "Biotransformation and Clearance of 3-(Phenylamino)propane-1,2-diol, a Compound Present in Samples Related to Toxic Oil Syndrome, in C57BL/6 and A/J Mice", Chem. Res. Toxicol., 12:1127-1137.
Zeinalova et al. (1977) "Inhibition of the oxidation of synthetic oils at high temperatures", Chemistry and Technology of Fuels and Oils, 13:40-42.

(Continued)

*Primary Examiner* — Matthew R Diaz
(74) *Attorney, Agent, or Firm* — Kagan Binder PLLC

(57) ABSTRACT

Described are compounds, compositions, and methods that include a nitrogen- and oxygen-containing aromatic compound, such as an aminophenol-based compound, which can be used for inhibiting polymerization of a monomer (e.g., styrene) composition. The compound includes a tertiary amine group wherein the nitrogen is attached to carbon-containing groups, and at least one of oxygen atom separated from the nitrogen by one or more carbon atoms. The antipolymerant can provide excellent antipolymerant activity in a monomer-containing composition.

22 Claims, 1 Drawing Sheet

(56) References Cited

U.S. PATENT DOCUMENTS

| | | | |
|---|---|---|---|
| 5,476,973 A | 12/1995 | Hatano et al. | |
| 5,583,247 A | 12/1996 | Nesvadba et al. | |
| 5,728,872 A * | 3/1998 | Riemenschneider | C07C 51/50 |
| | | | 562/598 |
| 5,763,144 A | 6/1998 | Jeganathan | |
| 5,909,337 A | 6/1999 | Tyndall, III | |
| 6,024,769 A | 2/2000 | Cotteret | |
| 6,040,482 A * | 3/2000 | Harris | C07C 215/76 |
| | | | 564/442 |
| 6,200,461 B1 * | 3/2001 | Eldin | C07C 7/20 |
| | | | 203/8 |
| 6,452,020 B1 | 9/2002 | Batlaw et al. | |
| 6,639,026 B2 * | 10/2003 | Eldin | C08F 2/40 |
| | | | 526/348.3 |
| 7,045,647 B2 | 5/2006 | Benage | |
| 7,204,858 B2 | 4/2007 | Desenne et al. | |
| 7,498,467 B2 * | 3/2009 | Shiraki | C08K 5/18 |
| | | | 564/355 |
| 7,569,615 B2 | 8/2009 | Leinweber et al. | |
| 7,671,098 B2 | 3/2010 | Leinweber et al. | |
| 7,900,590 B2 | 3/2011 | Cleveland et al. | |
| 7,902,317 B2 | 3/2011 | Kumar et al. | |
| 8,530,397 B2 | 9/2013 | Bera et al. | |
| 9,168,217 B2 | 10/2015 | Schweinsberg | |
| 9,212,330 B2 | 12/2015 | Bolton et al. | |
| 9,266,797 B2 | 2/2016 | Colorado, Jr. et al. | |
| 10,308,886 B2 * | 6/2019 | Rana | C10G 29/26 |
| 2001/0050700 A1 | 12/2001 | Smith et al. | |
| 2002/0156136 A1 | 10/2002 | Holtrup et al. | |
| 2003/0065177 A1 | 4/2003 | Sheridan et al. | |
| 2003/0111331 A1 | 6/2003 | Chalfant et al. | |
| 2003/0217418 A1 | 11/2003 | Fadel et al. | |
| 2004/0211702 A1 * | 10/2004 | Link | C09K 15/20 |
| | | | 252/403 |
| 2005/0209117 A1 | 9/2005 | Friedrich et al. | |
| 2008/0045666 A1 | 2/2008 | Snell et al. | |
| 2008/0090742 A1 | 4/2008 | Mathur | |
| 2012/0056128 A1 * | 3/2012 | Thoret Bauchet | C08F 2/42 |
| | | | 252/183.12 |
| 2019/0117541 A1 | 4/2019 | Consoli et al. | |
| 2020/0172831 A1 | 6/2020 | Dhawan et al. | |
| 2020/0339503 A1 | 10/2020 | Dhawan et al. | |
| 2020/0339880 A1 | 10/2020 | Masere et al. | |

FOREIGN PATENT DOCUMENTS

| | | |
|---|---|---|
| DE | 343151 C | 10/1921 |
| EP | 0145588 | 6/1985 |
| EP | 0449546 A1 | 10/1991 |
| ES | 145588 A2 * | 11/1984 |
| GB | 748856 A * | 5/1956 |
| GB | 2030581 A | 4/1980 |
| GB | 1567047 | 5/1980 |
| JP | 6340570 | 12/1994 |
| RU | 2046804 C1 * | 10/1995 |
| RU | 2046804 C1 | 10/1995 |
| WO | 2005037206 A2 | 4/2005 |
| WO | 2020113218 A2 | 6/2020 |

OTHER PUBLICATIONS

Habib et al. (2012) "Synthesis of Some Novel Antioxidantand Anticorrosive Additives for Egyptian Lubricating Oils" Petroleum Science and Technology, 30:2435-2449.

Ionova et al. (2011) "Synthesis, Structure, and Properties of New Antioxidants Based on Hydroxypropylated p-Aminodiphenylamine", Petroleum Chemistry, 51(6):454-457.

* cited by examiner

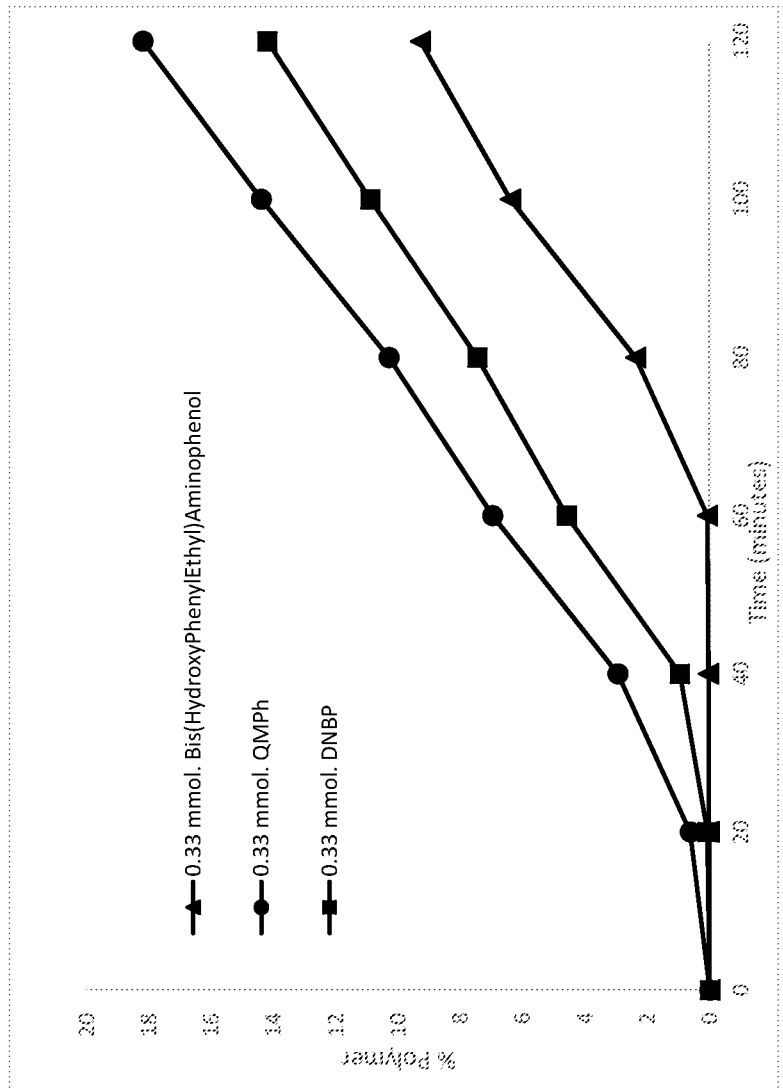

OXYGENATED AMINOPHENOL COMPOUNDS AND METHODS FOR PREVENTING MONOMER POLYMERIZATION

CROSS REFERENCE TO RELATED APPLICATION

This application claims the benefit of U.S. Provisional Patent Application Ser. No. 62/840,109 filed Apr. 29, 2019, the disclosure of which is incorporated by reference herein in its entirety.

TECHNICAL FIELD

The invention is directed to compositions and use of a nitrogen- and oxygen-containing aromatic antipolymerant compound for preventing premature polymerization of monomers.

BACKGROUND

The high-temperature processing of hydrocarbon stream laden with ethylenically unsaturated monomers like styrene, isoprene, butadiene, for instance can be very challenging. In various chemical industrial processes, the use of high temperatures to purify said monomers can lead to unwanted and problematic polymers. These vinylic monomers undesirably polymerize through radical polymerization especially at elevated temperatures. Similarly, transportation and storage of hydrocarbon streams containing vinylic species can lead to premature polymerization unless antipolymerants are added to said streams. The polymer thus formed can precipitate from solution to foul the process equipment. Removing the foulants becomes necessary. The physical removal or cleaning of the fouled equipment is often expensive. These undesirable polymerization reactions also result in a loss in the production efficiency and the consumption of valuable products. Undesired polymerization reactions are particularly problematic in compositions having vinyl aromatic monomers To prevent undesired polymerization reactions, free-radical polymerization inhibitors as antipolymerants are often added to process streams or stored compositions. However, these compounds are generally consumed quite rapidly. For example, in cases of emergency due to a mechanical or processing problems and where more inhibitor cannot be added, previously added inhibitor will be rapidly consumed. Subsequently, unwanted polymerization reactions will then rapidly recur.

Examples of polymerization inhibitors known in the art include dialkylhydroxylamines, such as hydroxypropylhydroxylamine (HPHA), and stable nitroxide free radicals. Other inhibitors include N,N'-dialkylphenylenediamines, N,N'-diarylphenylenediamines and N-aryl-N'-alkylphenylene-diamines. Quinone diimide compounds are also another class of inhibitors, However, nitroxide-containing compounds can release $NO_x$, making their use undesirable in some situations.

Other types of antipolymerant compounds often referred to as "retarders" slow down the rate of polymerization reactions. However, they are often not as effective as polymerization inhibitors, particularly stable nitroxide free radicals. Polymerization retarders, however, are usually not consumed as quickly as polymerization inhibitors so they tend to be more useful in cases of emergency shutdowns.

Retarders such as sulfur and dinitrophenol (DNP) compounds exemplified by 2,6-dinitrophenol, 2,4-dinitrocresol, and 2-sec-butyl-4,6-dinitrophenol (DNBP), were initially used. However DNP and sulfur retarders release $NO_x$ and $SO_x$ emissions, making their use problematic. Furthermore, DNP-based retarders are highly toxic such that the safety of personnel handling DNP-based antipolymerants is a major concern.

One class of compounds designed to function as a safer substitute for DNP retarders is based on quinone methide chemistry. Quinone methides slow the rate of polymer formation under static conditions and do not need to be frequently re-fed into the process stream. Some quinone methide compounds, however, do not exhibit good stability. Examples of quinone methide compounds are in U.S. Pat. Nos. 4,003,800, 5,583,247, and 7,045,647. The production of styrene typically involves the use of both an inhibitor (e.g., a nitroxide-containing inhibitor such as TEMPO) and a retarder (e.g., a quinone methide). While it is desired in various styrene production situations to eliminate the nitroxide-containing inhibitor, the use of only a retarder has been found to provide insufficient polymerization inhibition, making it difficult to eliminate or minimize inhibitor use.

Technical challenges remain in this area of technology relating to efficacy of compounds used to inhibit or slow polymerization reactions, as well as stability and safety concerns. In spite of the concerns over toxicity, DNP-based antipolymerants remain the most efficient retarders available. Out of safety concerns, there is a need for antipolymerants that are at least as efficacious as DNP-type retarders, but non-toxic.

SUMMARY

The current disclosure is directed to nitrogen- and oxygen-containing aromatic compounds, such as aminophenol compounds, that include a tertiary amine chemistry, as well as compositions and methods that include or utilize the aminophenol compound as an antipolymerant to inhibit the polymerization of ethylenically unsaturated monomers like styrene and butadiene in various processes and situations, such as purification, fractionation, separation, compression, transportation, and storage of various monomer-containing compositions.

The use of the inventive antipolymerant compositions mitigates the fouling of process, transportation and storage equipment, while at the same time avoiding the drawbacks of using certain antipolymerants that release undesirable emissions and/or are toxic. In turn, polymer contamination of purified monomer products can be drastically reduced and maintenance costs of said equipment minimized using aminophenol antipolymerants of the disclosure.

In embodiments, the disclosure provides a method for inhibiting the polymerization of monomers in a monomer-containing composition, or a composition that is capable of forming monomer. The method includes a step of adding a nitrogen- and oxygen-containing aromatic antipolymerant to a composition comprising polymerizable monomer, or capable of forming a polymerizable monomer, the antipolymerant being a compound of Formula I:

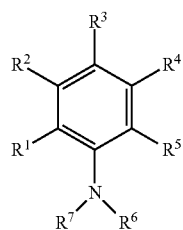

(I)

wherein at least one of —R¹, —R², —R³, —R⁴, and —R⁵ is or are —OR⁸ wherein R⁸ is selected from the group consisting of H and alkyl, aryl, alkyl-aryl, and aryl-alkyl having 3-18 carbon atoms, wherein R⁶ and R⁷ are independently carbon-containing groups, and at least one of R⁶ and R⁷ comprises one or more oxygen atom(s) separated from the N atom by one or more carbon atoms. In Formula I any one or more of —R¹, —R², —R³, —R⁴, and —R⁵ that is not —OR⁸ is or are selected from the group consisting of hydrogen, alkyl, aryl, alkyl aryl and aryl alkyl, or any two adjacent groups of —R¹, —R², —R⁴, and —R⁵ that are not —OR⁸ form one or more ring structures. In embodiments, the one or more oxygen atom(s) in R⁶ and/or R⁷ are separated from the N atom by two or more carbon atoms.

In embodiments, the oxygen atom(s) in R⁶ and/or R⁷ are present in the form of a hydroxyl group(s), an ether group(s), or both. For example, R⁶ and/or R⁷ can be of the formula: —R⁹OR¹⁰, wherein R⁹ is hydrocarbylene group, optionally substituted, and R⁹ is hydrocarbyl group, optionally substituted. As another example, R⁶ and/or R⁷ include an ether group(s) and a hydroxyl group(s). For example, R⁶ and/or R⁷ can be of the formula: —R⁹OR¹⁰, wherein R⁹ is hydroxylated hydrocarbylene group group, and R¹⁰ is hydrocarbyl group. In yet other embodiments, one or both of R⁶ and R⁷ is/are a hydroxylated hydrocarbyl group.

In other embodiments, the disclosure provides a composition including a compound of Formula II,

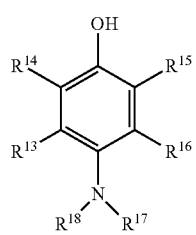

(II)

wherein any one or more of —R¹³, —R¹⁴, —R¹, and —R¹⁶ are independently hydrogen, alkyl, aryl, alkyl aryl and aryl alkyl, or any two adjacent groups of —R¹³, —R¹⁴, —R¹⁵, and —R¹⁶ form one or more ring structures, wherein R¹⁷ and R¹⁸ the same and selected from the group consisting of

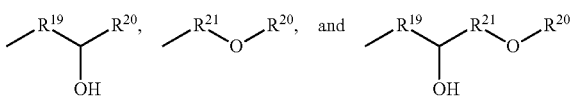

wherein R¹⁹ is (-) or (CH₂)ᵧ—, wherein y is an integer in the range of 1-3; wherein R²⁰ is selected from C1-C12 unsubstituted alkyl, aryl, alkyl aryl and aryl alkyl; and wherein R²¹ is —(CH₂)_z—, wherein z is an integer in the range of 1-6 compounds of Formula II, In embodiments, the nitrogen- and oxygen-containing aromatic antipolymerant of Formula I or II can be provided in a composition for addition to a monomer-containing composition, or a composition that is capable of forming monomer. For example, the composition can include a solvent and solid component consisting essentially of the nitrogen- and oxygen-containing aromatic antipolymerant of Formula I or II.

In embodiments, the nitrogen- and oxygen-containing aromatic antipolymerant can be used without, or with very little, nitroxyl-based based antipolymerant, yet it still provides excellent ability to inhibit polymerization of monomers in solution.

Advantageously, nitrogen- and oxygen-containing aromatic compounds of the disclosure can exhibit characteristics of both a polymerization inhibitor and a polymerization retarder, such as described herein. For example, compounds of the disclosure can inhibit formation of polymer from those monomers during an induction time, and then after the induction time reduce the rate at which the formation of the polymer occurs relative to the rate at which it would have formed in the absence of the polymerization retarder. This is beneficial, as antipolymerant methods can be performed without having to use different types of antipolymerant compounds, such as in mixture or added to a monomer-containing composition at different times. In turn this can streamline operations and reduce processing and materials costs, as well as improving monomer-containing composition quality as fewer compounds are required to he added.

DESCRIPTION OF TRE DRAWING

The FIGURE is a graph of the amount of polystyrene polymer formed from styrene monomer solutions in the presence an aminophenol antipolymerant of the disclosure, and comparative antipolymerants (QMPh, and DNBP) at 120° C. For each molecule, the novel compounds simultaneously perform as both inhibitor and retarder.

DETAILED DESCRIPTION

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Additional advantages and novel features of the invention will be set forth in part in the description that follows, and in part will become apparent to those skilled in the art upon examination of the following, or may be learned through routine experimentation upon practice of the invention.

The disclosure provides methods and compositions that include a nitrogen- and oxygen-containing aromatic antipolymerant to prevent unwanted formation of polymer. The nitrogen- and oxygen-containing aromatic antipolymerant compounds provide excellent antipolymerant activity similar to many nitroxyl-containing antipolymerants. As such, methods of the disclosure do not necessarily require the simultaneous addition of a nitroxyl-containing antipolymerants for treatment of a monomer stream, although in some modes of practice a nitroxyl-containing antipolymerant can be used with a nitrogen- and oxygen-containing aromatic antipolymerant if desired.

The efficacy of the nitrogen- and oxygen-containing aromatic compounds of the disclosure allows greater flexibility for inhibiting polymerization of a monomer composition, such as when the certain conditions are desired (e.g., when use of a nitroxyl-containing antipolymerant is not recommended, such as when it is desired to minimize or eliminate $NO_x$ emissions in a monomer-containing composition).

A composition that includes the nitrogen- and oxygen-containing aromatic antipolymerant and any one or more optional component can be in a desired form, such as in a liquid form, a dry form, or as a suspension or dispersion, The nitrogen- and oxygen-containing aromatic antipolymerant can be in a desired physical state in the composition, such as in a dissolved state, in a partially dissolved state, in a suspended state, or in a dry mixture. Also, the nitrogen- and oxygen-containing aromatic antipolymerant can be in desired forms in the composition, such as optionally in particulate forms. if the nitrogen- and oxygen-containing aromatic antipolymerant is in a particulate form, the particles can optionally be described in terms of particle size (e.g., particles of a size range) and/or shape. The form of the composition and the state of the component(s) therein can be chosen by selection of the nitrogen- and oxygen-containing aromatic antipolymerant, with an understanding of its physical properties.

"Antipolymerants" broadly refer to "polymerization inhibitors" and "polymerization retarders" which are compounds that generally inhibit or reduce the formation of polymers from one or more radically polymerizable compounds.

A "polymerization inhibitor," in the presence of polymerizable monomers, inhibits the formation of a polymer from those monomers during an induction time. After the induction time has lapsed, the polymer's formation occurs at substantially the same rate as it does in the absence of the polymerization inhibitor. Nitroxyl-containing compounds like HTEMPO are considered polymerization inhibitors.

A "polymerization retarder," does not exhibit an induction time, but instead once added to a polymerizable monomer composition reduces the rate at which the formation of the polymer occurs relative to the rate at which it would have formed in the absence of the polymerization retarder. Quinone methide compounds are examples of polymerization retarders.

Polymerization inhibitors, as opposed to polymerization retarders, are generally consumed rapidly. Polymerization retarders, while they slow down the rate of polymerization reactions, are not as effective as polymerization inhibitors. Polymerization retarders, however, are usually not consumed as quickly as polymerization inhibitors.

In embodiments, nitrogen- and oxygen-containing aromatic compounds of the disclosure can exhibit characteristics of a polymerization inhibitor, a polymerization retarder, or both a polymerization inhibitor and retarder. The use of a single compound having both polymerization inhibitor and retarder characteristics can be particularly beneficial as it may reduce the need, in some modes of practice, to include a different antipolymerant compound(s) in a monomer-containing composition. However, it is understood that antipolymerant compositions of the disclosure are not limited to use or presence of a single compound with inhibitor/retarder characteristics, but can optionally be used with other types of antipolymerants, such as those known in the art, if desired.

The form of the composition and the state of the component(s) therein can also be affected by the inclusion of one or more optional components, such as a solvent, or solvent mixture, or other excipient compounds like surfactants, dispersants, etc. The form of the composition and the state of the components therein can also be affected by temperature, and composition properties may optionally be described in circumstances at a particular temperature (e.g., at a storage temperature such as 5° C. or below, at room temperature (25° C.), or at a temperature used for monomer synthesis and/or processing (e.g., about 100° C. or greater, about 150° C., about 175° C., etc).

As noted, a nitrogen- and oxygen-containing aromatic antipolymerant composition can include other components such as a solvent, surfactants, dispersants, etc. Ii an optional component is present in the composition, it may be described in terms of a weight amount relative to the nitrogen- and oxygen-containing aromatic antipolymerant. The optional component(s) may be present in a weight amount greater than, in an amount about the same as, or an amount less than the nitrogen- and oxygen-containing aromatic antipolymerant.

As used herein, the term "optional" or "optionally" means that the subsequently described object (e.g., compound), event (e.g., processing step), or circumstance may, but need not occur, and that the description includes instances where the object, event, or circumstance occurs and instances in which it does not.

Compositions of the disclosure can include those recited compounds and optionally can include other components in the composition but in very small amounts (e.g., described in terms of a composition "consisting essentially of" the recited components). For example, such compositions can include one or more other components but not in an amount that is greater than about 1% (wt), greater than about 0.5% (wt), greater than about 0.1% (wt), or greater than about 0.01% (wt), of the total composition. A composition that consists essentially of a solid component that is the nitrogen- and oxygen-containing aromatic antipolymerant (for example, dissolved in a solvent) can optionally include one or more other (e.g., solid) components but in an amount less than about 1% (wt) of the total composition weight. In a composition "consisting of" the recited components there is no other measurable amount of component other than the recited component. In some embodiments, a nitroxyl-containing antipolymerant can optionally be present in an amount of less than 1% (wt), less than 0.5% (wt), less than 0.1% (wt), or less than 0.01% (wt), of the total composition, and more preferably a nitroxyl-containing antipolymerant is not present in a detectable level in the composition.

As used herein, the terms "substantially" and "consisting essentially of" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, dispersibility, stability, rate, solubility, and the like; intended values include weight of a component added, concentration of components added, and the like. The effect on methods that are modified include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" or "consisting essentially of", the claims appended hereto include equivalents to these types and amounts of materials.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any, range of values, for example "about 1 to 5" the recitation means "1 to 5" and "about 1 to about 5" and "1 to about 5" and "about 1 to 5" unless specifically limited by context.

Compositions and methods of the disclosure include or use an antipolymerant that has a tertiary nitrogen- and oxygen-containing aromatic chemistry. The nitrogen- and oxygen-containing aromatic antipolymerant includes, in the least, an unsaturated 6 carbon ring structure having one or more hydroxyl or alkoxy groups bonded to a ring carbon atom(s), and a nitrogen atom of a tertiary amine group bonded to another ring carbon, with the nitrogen atom of the tertiary amine group attached to a first carbon-containing group and a second carbon-containing group, wherein at least of the first and/or second carbon-containing group(s) include an oxygen atom which is separated from the nitrogen atom of the tertiary amine group by one or more carbon atoms. For example, the oxygen atom is separated from the nitrogen atom by one carbon atom, by preferably two carbon atoms, by preferably three carbon atoms, by four carbon atoms, or by five carbon atoms.

The portion of the unsaturated 6 carbon ring structure having one or more hydroxyl or alkoxy groups may consist of an aryl ring or can be part of a fused ring structure that includes an unsaturated 6 carbon ring structure. Preferred nitrogen- and oxygen-containing aromatic antipolymerants use a 6 carbon ring structure, such as phenol, pyrocatechol, resorcinol, hydroquinone, hydroxyhydroquinone, or phlorolucitol. However, the nitrogen- and oxygen-containing aromatic may also be based on hydroxyl-containing fused aromatic chemistries such as naphthol, hydroxyanthracene, or indenol.

In embodiments, the first and/or second carbon-containing group(s) include a single oxygen atom in the form of an ester group, or in the form of a hydroxyl group. In other embodiments the first and/or second carbon-containing group(s) includes two oxygen atoms, such as one in the form of an ester group, and one in the form of a hydroxyl group.

In embodiments, the first and/or second carbon-containing group(s) include: a number of carbon atoms in the range of 1 to about 18, 2 to about 16, or 3 to about 12; a number of hydrogen atoms in the range of 3 to about 40, 5 to about 30, or 7 to about 25; a number of oxygen atoms of 1, 2, 3, or 4; or any combination thereof. In preferred embodiments, the carbon containing groups include only carbon, oxygen, and hydrogen.

Preferred nitrogen- and oxygen-containing aromatic compounds of the current disclosure are "bis" nitrogen- and oxygen-containing aromatics, that is, nitrogen- and oxygen-containing aromatics wherein the first carbon-containing group and the second carbon-containing group bonded to the nitrogen atom of the tertiary amine group are the same. For example, in the aminophenol compound 4-bis[(6-ethoxyhexyl)amino]phenol the first and second carbon-containing groups are the same and are $(CH_2)_2O(CH_2)_5CH_3$.

Other "non-bis" nitrogen- and oxygen-containing aromatics are contemplated, such as those wherein the first and second carbon-containing groups are different, with the proviso that at least one carbon-containing group includes an oxygen atom separated from the nitrogen atom of the tertiary amine by at least one, and preferably two or more, carbon atoms. Exemplary "non-bis" compounds can include those wherein the first carbon-containing groups is selected from ether- and carbon-containing groups, hydroxyl- and carbon-containing groups, and hydroxyl-, ether-, and carbon-containing groups, and the second carbon-containing group is selected from a hydrocarbyl group (not containing oxygen), such as alkyl (linear, branched, cyclic), aryl, alkyl aryl, and aryl alkyl. Other exemplary "non-bis" compounds can include those wherein both the first and second carbon-containing groups include one or more oxygen atoms, but that have different chemistries. For example, the first and second carbon-containing groups can be selected from ether- and carbon-containing groups, hydroxyl- and carbon-containing groups, and hydroxyl-, ether-, and carbon-containing groups, with the proviso that the first and second carbon-containing groups have different chemistries. Different chemistries can be reflected by different isomeric forms of an oxygen- and carbon-containing group.

Nitrogen- and oxygen-containing aromatic compounds of the current disclosure can be described with reference Formula I:

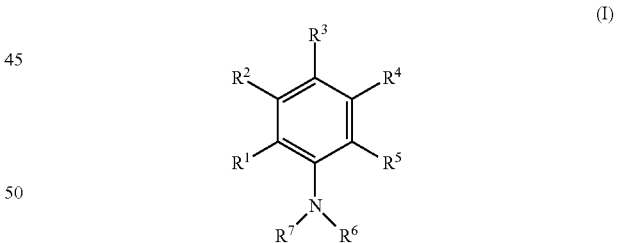

wherein at least one of $-R^1$, $-R^2$, $-R^3$, $-R^4$, and $-R^5$ is or are $-OR^8$, wherein $R^8$ is selected from the group consisting of $-H$ and alkyl, aryl, alkyl-aryl, and aryl-alkyl having 3-18 carbon atoms, and wherein $R^6$ (e.g., the first carbon-containing group) and $R^7$ (e.g., the first carbon-containing group) are independently carbon-containing groups, and at least one of $R^6$ and $R^7$ comprises one or more oxygen atom(s) separated from the N atom by one or more carbon atoms; wherein any one or more of $-R^1$, $-R^2$, $-R^3$, $-R^4$, and $-R^5$ and that is not $-OR^8$ is or are selected from the group consisting of hydrogen, alkyl, aryl, alkyl aryl and aryl alkyl, or any two adjacent groups of $-R^1$, $-R^2$, $-R^3$, $-R^4$, and $-R^5$ that are not $-OR^8$ form one or more ring structures.

In embodiments, one or more of —R$^1$, —R$^2$, —R$^3$, —R$^4$, and —R$^5$ is or are —OH, and —R$^1$, —R$^2$, —R$^3$, —R$^4$, and —R$^5$ that are not —OH are —H. As such, Formula I can be based on compounds such as aminophenol, aminopyrocatechol, aminoresorcinol, aminohydroquinone, aminohydroxyhydroquinone, and aminophlorolucitol.

Alternatively, two adjacent groups of —R$^1$, —R$^2$, —R$^3$, —R$^4$, and —R$^5$ that are not —OH form one or more ring structures, for example the compound can include a bicyclic or a tricyclic structure, including one, two, or three 6-membered rings, or a 6-membered ring fused to a 5-membered ring. For example, the nitrogen- and oxygen-containing aromatic can be based on hydroxyl-containing fused aromatic chemistries such as aminonaphthol, aminohydroxyanthracene, or aminoindenol.

In embodiments, the nitrogen- and oxygen-containing aromatic compounds of the disclosure include an ether chemistry wherein one or both of R$^6$ and R$^7$ are of the formula: —R$^9$OR$^{10}$. In —R$^9$OR$^{10}$, R$^9$ is hydrocarbylene group, optionally substituted (such as with an alkyl group, alkoxy group, etc.,), and R$^{10}$ is hydrocarbyl group, optionally substituted. One or both of R$^9$ and R$^{10}$ can have an amount of carbon atoms in the range of 1-18, 1-12, 1-8, 1-6, or 1-3.

In embodiments, R$^9$ is of the sub-formula —(CR$^{24}$R$^{25}$)$_s$—, wherein R$^{24}$R$^{25}$ are independently selected from H, R$^{10}$, and OR$^{10}$, wherein s is an integer in the range of 1-12, 1-6, or preferably 1-3.

For example, R$^9$ can be a linear or branched C1-C6 hydrocarbylene group, such as one selected from the group consisting of methylene, ethylene, propylene, isopropylene, butylene, isobutylene, sec-butylene, tert-butylene, pentylene, and hexylene.

For example, R$^{10}$ can be selected from linear, branched, or cyclic alkyl, aryl, alkyl-aryl, and aryl-alkyl C1-C12 groups. Preferred R$^{10}$ groups include those such as :methyl, ethyl, propyl, isopropyl, butyl, isobutyl, sec-butyl, Cert-butyl, pentyl, cyclopentyl, isopentyl, neopentyl, hexyl, cyclohexyl, 1-, 2-, and 3-methylbutyl, 1,1-, 1,2-, or 2,2-dimethylpropyl, 1-ethyl-propyl, 1-, 2-, 3-, or 4-methylpentyl, 1,1-, 1,2-, 2,2-, 2,3-, or 3,3-dimethylbutyl, 1- or 2-ethylbutyl, 1-ethyl-1-methylpropyl, and 1,1,2- or 1,2,2-trimethylpropyl, methylcyclopentyl; heptyl, 2-methylhexyl, 3-methylhexyl, 4-methylhexyl, 5-methylhexyl, 3-ethylpentyl, 2,2,3-trimethylbutyl, 2,2-dimethylpentyl, 2,3-dimethylpentyl, 2,4-dimethylpentyl, 3,3-dimethylpentyl, 3,4-dimethylpentyl, dimethylpentyl, cycloheptyl, 1-methylcyclohexyl, and 2-methylcyclohexyl; octyl, 2-methylheptyl 3-methylheptyl, 4-methylheptyl, 2-ethylhexyl, 3-ethylhexyl, 4-ethylhexyl, 5-ethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethyl-2-methylpentyl, 3-ethyl-3-methylpentyl, 2,2,3-trimethylpentyl, 2,2,4-trimethylpentyl, 2,3,3-trimethylpentyl, 2,3,4-trimethylpentyl, and 2,2,3,3-tetramethylbutyl.

In exemplary embodiments, the nitrogen- and oxygen-containing aromatic antipolymerant is a compound selected from the group consisting of:

4-bis[(methoxymethyl)amino]phenol, 4-bis[(2-methoxyethyl)amino]phenol, 4-bis[(3-methoxypropyl)amino]phenol, 4-bis[(4-methoxybutyl)amino]phenol 4-bis[(5-methoxypentyl)amino]phenol, 4-bis[(6-methoxyhexyl)amino]phenol, 4-bis[(methoxyphenyl)amino]phenol;

4-bis[(ethoxymethyl)amino]phenol, 4-bis[(2-ethoxyethyl)amino]phenol, 4-bis[(3-ethoxypropyl)amino]phenol, 4-bis[(4-ethoxybutyl)amino]phenol, 4-bis[(5-ethoxypentyl)amino]phenol, 4-bis[(6-ethoxyhexyl)amino]phenol, 4-bis[(ethoxyphenyl)amino]phenol;

4-bis[(propoxymethyl)amino]phenol, 4-bis[(2-propoxyethyl)amino]phenol, 4-bis[(3-propoxypropyl)amino]phenol, 4-bis[(4-propoxybutyl)amino]phenol, 4-bis[(5-propoxypentyl)amino]phenol, 4-bis[(6-propoxyhexyl)amino]phenol, 4-bis[(propoxyphenyl)amino]phenol;

4-bis[(butoxymethyl)amino]phenol, 4-bis[(2-butoxyethyl)amino]phenol, 4-bis[(3-butoxypropyl)amino]phenol, 4-bis[(4-butoxybutyl)amino]phenol, 4-bis[(5-butoxypentyl)amino]phenol, 4-bis[(6-butoxyhexyl)amino]phenol, and 4-bis[(butoxyphenyl)amino]phenol.

In some embodiments, in the nitrogen- and oxygen-containing aromatic compounds of Formula 1, one or both of R$^6$ and R$^7$ include both ether and hydroxyl groups. For example, one or both of R$^6$ and R$^7$ are of the formula: —R$^9$OR$^{10}$, where R$^9$ is a hydroxylated hydrocarbylene group, and R$^{10}$ is hydrocarbyl group, optionally substituted. example, R$^9$ can be C1-C8 hydrocarbylene with a single hydroxyl group, such as one selected from the group consisting of:

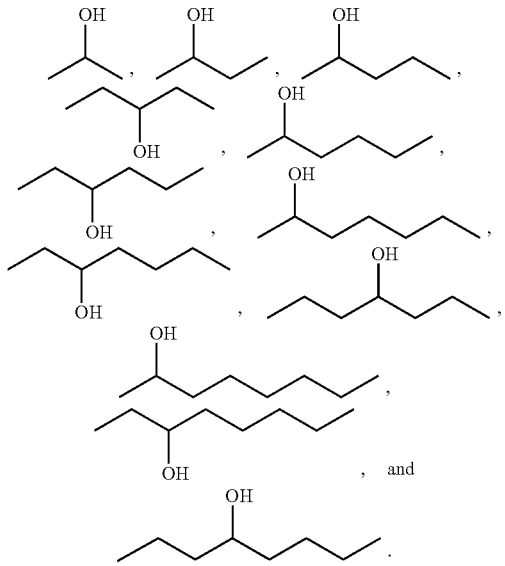

In some embodiments, exemplary species of ether and hydroxylated hydrocarbylene groups of the formula —R$^9$OR$^{10}$ include the following groups:

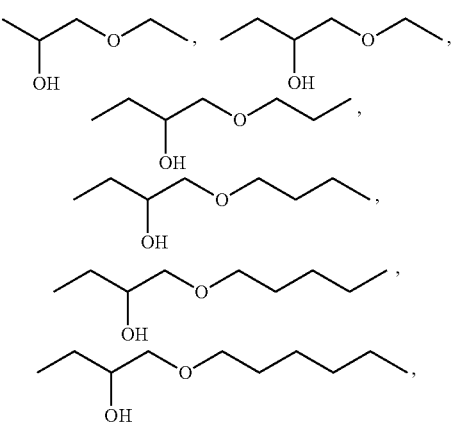

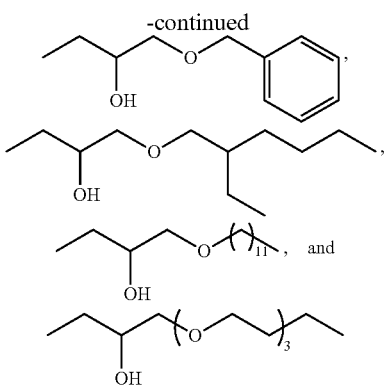

In exemplary embodiments, the nitrogen- and oxygen-containing aromatic antipolymerant having ether and hydroxylated hydrocarbylene group can be a compound selected from the group consisting of:

4-bis[(2-methoxy-1-hydroxy-ethyl)amino]phenol, 4-bis[(3-methoxy-2-hydroxy-propyl)amino]phenol, 4-bis[(4-methoxy-2-hydroxy-butyl)amino]phenol, 4-bis[(5-methoxy-2-hydroxy-pentyl)amino]phenol, 4-bis[(6-methoxy-2-hydroxy-hexyl)amino]phenol, 4-bis[(methoxyhydroxyphenyl)amino]phenol;

4-bis[(2-ethoxy-1-hydroxy-ethyl)amino]phenol, 4-bis[(3-ethoxy-2-hydroxy-propyl)amino]phenol, 4-bis[(4-ethoxy-2-hydroxy-butyl)amino]phenol, 4-bis[(5-ethoxy-2-hydroxy-pentyl)amino]phenol, 4-bis[(6-ethoxy-2-hydroxy-hexyl)amino] phenol, 4-bis[(ethoxyhydroxyphenyl)amino]phenol;

4-bis[(2-propoxy-1-hydroxy-ethyl)amino]phenol, 4-bis[(3-propoxy-2-hydroxy-propyl)amino]phenol, 4-bis[(4-propoxy-2-hydroxy-butyl)amino]phenol, 4-bis[(5-propoxy-2-hydroxy-pentyl)amino]phenol, 4-bis[(6-propoxy-2-hydroxy-hexyl)amino]phenol, 4-bis[(propoxyhydroxyphenyl) amino]phenol, 4-bis[(2-butoxy-1-hydroxy-ethyl)amino]phenol, 4-bis[(3-butoxy-2-hydroxy-propyl)amino]phenol, 4-bis[(4-butoxy-2-hydroxy-butyl)amino]phenol, 4-bis[(5-butoxy-2-hydroxy-pentyl)amino]phenol, 4-bis[(6-butoxy-2-hydroxy-hexyl)amino] phenol, and 4-bis[(butoxyhydroxyphenyl)amino]phenol In some embodiments, in the nitrogen- and oxygen-containing aromatic compounds of Formula I, one or both of $R^6$ and $R^7$ is or are a hydroxylated hydrocarbyl group(s). Exemplary hydroxylated hydrocarbyl group(s) can have an amount of carbon atoms in the range of 1-18, 1-12, 1-8, 1-6, or 1-3, and can be selected from hydroxylated linear, branched, and cyclic alkanol, hydroxylated aryl, hydroxylated alkyl-aryl, and hydroxylated aryl-alkyl.

In some embodiments, the hydroxylated hydrocarbyl group is of the formula

In embodiments, $R^9$ is of the sub-formula $-(CR^{24}R^{25})_q(CHOH)(CH_2)_zR^{11}$, wherein $R^{24}$ and $R^{25}$ are independently selected from H, $R^{10}$, and $OR^{10}$, wherein q and z are independently (-): a covalent bond, or an integer in the range of 1-12, preferably (-) or an integer in the range of 1-6 or 1-3, and wherein $R^{11}$ is selected from the group consisting of $R^{10}$, as described herein, and

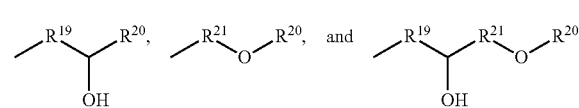

wherein $R^{12}$ is independently selected from the group consisting of H and $R^{10}$, as described herein, and wherein q is an integer in the range of 1-5. In some embodiments, $R^9$ is of the sub-formula $-(CH_2)_q(CHOH)(CH_2)_zR^{11}$, wherein the variables have the meanings given herein.

In exemplary embodiments, the nitrogen- and oxygen-containing aromatic antipolymerant having ether and hydroxylated hydrocarbylene group can be a compound selected from the group consisting of:

4-bis[(hydroxymethyl)amino]phenol 4-bis[(1-hydroxyethyl)amino]phenol, 4-bis[(2-hydroxyethyl)amino]phenol 4-bis[(1-hydroxypropyl)amino]phenol, 4-bis[(2-hydroxypropyl)amino] phenol, 4-bis[(3-hydroxypropyl)amino]phenol, 4-bis[(1-hydroxybutyl)amino]phenol, 4-bis[(2-hydroxybutyl)amino]phenol, 4-bis[(3-hydroxybutyl)amino]phenol, 4-bis[(4-hydroxybutyl)amino]phenol, 4-bis[(1-hydroxypentyl)amino]phenol, 4-bis[(2-hydroxypentyl)amino] phenol, 4-bis[(3-hydroxypentyl)amino]phenol, 4-bis[(4-hydroxypentyl)amino] phenol, 4-bis[(5-hydroxypentyl)amino]phenol 4-bis[(1-hydroxyhexyl)amino]phenol, 4-bis[(2-hydroxyhexyl)amino]phenol, 4-bis[(3-hydroxyhexyl)amino]phenol, 4-bis[(4-hydroxyhexyl)amino]phenol, 4-bis[(5-hydroxyhexyl)amino]phenol, 4-bis[(6-hydroxyhexyl)amino]phenol, 4-bis[(1-hydroxyhexyl)amino]phenol, 4-bis[(2-hydroxyhexyl)amino]phenol, 4-bis[(3-hydroxyhexyl)amino] phenol, 4-bis[(4-hydroxyhexyl)amino]phenol, 4-bis[(5-hydroxyhexyl)amino]phenol, 4-bis[(6-hydroxyhexyl)amino]phenol, 4-bis[(2-hydroxy-2-phenylethyl)amino]phenol, 4-bis[(2-hydroxy-3-phenylpropyl)amino]phenol, 4-bis[(3-hydroxy-3-phenylpropyl)amino]phenol, 4-bis[(2-hydroxy-4-phenylbutyl)amino]phenol, 4-bis[(3-hydroxy-4-phenylbutyl)amino]phenol, and 4-bis[(4-hydroxy-4-phenylbutyl)amino] phenol.

The disclosure also provides compositions that include 4-bis-aminophenol compounds of: Formula II (which are a sub-genus of Formula I):

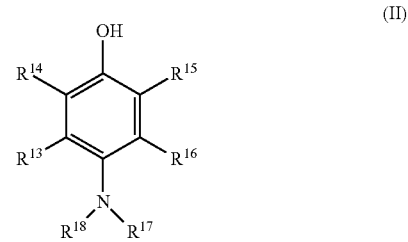

In Formula II, any one or more of $-R^{13}$, $-R^{14}$, $-R^{15}$, and $-R^{16}$ are independently selected from the group consisting of hydrogen, alkyl, aryl, alkyl aryl and aryl alkyl, or adjacent groups form one or more ring structures, and are preferably hydrogen, and $R^{17}$ and $R^{18}$ the same and selected from the group consisting of wherein $R^{19}$ is (-) or $-(CH_2)_y-$, wherein y is an integer in the range of 1-3; wherein $R^{20}$ is selected from C1-C12 unsubstituted alkyl, aryl, alkyl aryl and aryl alkyl; and wherein $R^{21}$ is —$(CH_2)_z$—, wherein z is an integer in the range of 1-6.

In some embodiments the disclosure provides a nitrogen- and oxygen-containing aromatic antipolymerant-containing composition that includes, or that can be added to, one or more polymerizable monomers, or one or more compounds that are capable of forming polymerizable monomers, wherein the composition includes an aminophenol antipolymerant of Formula I or II.

Nitrogen- and oxygen-containing aromatic compounds of the disclosure, including, aminophenol compounds as described herein, can be prepared using methods according to the disclosure. In some modes of practice, and as a general matter, an aryl-group containing reactant having primary amine and hydroxyl groups, such as 4-aminophenol, is reacted with a molar excess (e.g., a two molar excess) of a carbon and oxygen-containing reactant, capable of reaction with the primary amine groups to provide a product as described herein. The compounds can be reacted in an organic solvent such as an alcohol like methanol, butyl carbitol, and butyl glycol, with reflux at an elevated temperature (e.g., >100° C.).

In some modes of practice, the reactant includes an oxirane group as the amine-reactive group. Oxirane-containing reactants can include desired carbon chemistry and can also include additional oxygen atom(s), such as in the form of ether groups. Exemplary oxirane-containing reactants are glycidyl ethers, such as alkyl glycidyl ethers and alkyl glycidyl ethers.

In some modes of practice the oxirane-containing reactant is of formula III:

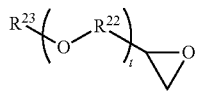

wherein $R^{22}$ is —$(CH_2)_w$—, wherein w is an integer in the range of 1-3, t is an integer in the range of 1-100, 1-50, 1-25, 1-15, 1-1.0, 1-5, or t is 2, 3, or 4, and wherein $R^{23}$ is $R^{10}$, as described herein, optionally substituted with one or more hydroxyl groups.

Nitrogen- and oxygen-containing aromatic compounds that can be used as antipolymerants are also described in commonly-assigned U.S. Provisional Patent Application Ser. No. 62/840,133, entitled "Oxygenated Aromatic Amines and Use as Antioxidants,", and filed Apr. 29, 2019, now U.S. Pub. No. 2020/0339503.

An amount of the nitrogen- and oxygen-containing aromatic antipolymerant, and any other (optional) component in a composition can be described in various ways, such as by a weight percentage (% wt.) or by molar amount of nitrogen- and oxygen-containing aromatic antipolymerant in the composition. When other components are used along with the nitrogen- and oxygen-containing aromatic antipolymerant, such compounds can also be described in terms of weight ratios, or in terms of relative amounts to one another, in a composition.

In some embodiments, a nitrogen- and oxygen-containing aromatic of any of Formulas I or II can be used without, or with minimal nitroxyl group containing antipolymerant. If a nitroxyl group containing antipolymerant is included, it can be present in very small amounts, such as in a composition comprising polymerizable monomer, wherein the nitroxyl group containing antipolymerant is not present at all, or present in a very small amount (less than 50 ppm).

For example, in a composition comprising polymerizable monomer and the nitrogen- and oxygen-containing aromatic antipolymerant, a nitroxyl group containing antipolymerant can optionally be present in an amount of less than 50 ppm, less than 25 ppm, less than 10 ppm, less than 5 ppm, less than 2.5 ppm, less than 2 ppm, less than 1.5 ppm, less than 1 ppm, less than 0.75 ppm, or less than 0.5 ppm.

Nitroxyl group-containing compounds trap propagating monomer radicals in thermally unstable species and inhibit polymerization. A nitroxyl/nitroxide group, which can also be referred to as an amine-N-oxide group, is a functional group including an NO bond and side groups attaching to the nitrogen. Nitroxide (nitroxyl) radicals are oxygen-centered radicals with the free electron delocalized over the N—O bond. Nitroxide-containing polymerization inhibitors can include N—O resonance structures that contributes to the stability of nitroxide radicals.

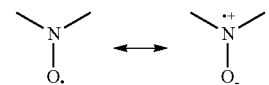

Exemplary nitroxide-containing compounds which are excluded from compositions from the disclosure, or are used in limited amounts, include, but are not limited to: 2,2,6,6-tetramethylpiperidinyl-1-oxyl (TEMPO), 4-hydroxy-2,2,6,6-tetramethylpiperidinyl-1-oxyl(HTMPO), 4-oxo-2,2,6,6-tetramethylpiperidinyl-1-oxyl (OTEMPO), di-tert-butyl nitroxyl, 1-oxyl-2,2,6,6-tetramethyl-4-n-propoxypiperidine, oxyl-2,2,6,6-tetramethyl-4-n-butoxypiperidine, 1-oxyl-2,2,6,6-tetramethyl-4-t-butoxypiperidine, 1-oxyl-2,2,6,6-tetramethyl-4-s-butoxypiperidine, 1-oxyl-2,2,6,6-tetramethyl-4-(2-methoxyethoxy)piperidine, 1-oxyl-2,2,6,6-tetramethyl-4-(2-methoxyethoxyacetoxy)piperidine, 1-oxyl-2,2,6,6-tetramethylpiperidin-4-yl stearate, oxyl-2,2,6,6-tetramethylpiperidin-4-yl acetate, 1-oxyl-2,2,6,6-tetramethylpiperidin-4-yl butyrate, 1-oxyl-2,2,6,6-tetramethylpiperidin-4-yl 2-ethylhexanoate, 1-oxyl-2,2,6,6-tetramethylpiperidin-4-yl octanoate, 1-oxyl-2,2,6,6-tetramethylpiperidin-4-yl laurate, oxyl-2,2,6,6-tetramethylpiperidin-4-yl benzoate, 1-oxyl-2,2,6,6-tetramethylpiperidin-4-yl 4-tert-butylbenzoate, 1-oxyl-2,2,6,6-tetramethyl-4-allyloxy-piperidine, 1-oxyl-2,2,6,6-tetramethyl-4-acetamidopiperidine, 1-oxyl-2,2,6,6-tetramethyl-4-(N-butylformamido)piperidine, N-(1-oxyl-2,2,6,6-tetramethylpiperidin-4-yl)-caprolactam, N-(1-oxyl-2,2,6,6-tetramethylpiperidin-4-yl)-dodecylsuccinimide, 1-oxyl-2,2,6,6-tetramethyl-4-(2,3-dihydroxypropoxy)piperidine, 1-oxyl-2,2,6,6-tetramethyl-4-(2-hydroxyl-4-oxapentoxy)piperidine, and mixtures thereof (See. for example, U.S. Pat. No. 9,266,797.) Any of these compounds can be present at very low amounts (less than 50 ppm, 25 ppm, 10 ppm, etc., as described herein) in a polymerizable monomer composition, or can be excluded from the composition altogether.

Other exemplary nitroxide-containing compounds include two or three nitroxyl groups. Such compounds may be bis- or tris-compounds. Exemplary bis-nitroxide and tris-nitroxide polymerization inhibitor compound include bis(1-oxyl-2,2,6,6-tetramethylpiperidin-4-yl) succinate, bis (1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis (1-oxyl-2,2,6,6-tetramethylpiperidin-4-yl) isophthalate, bis (1-oxyl-2,2,6,6-tetramethylpiperidin-4-yl) terephthalate, bis (1-oxyl-2,2,6,6-tetramethylpiperidin-4-yl) hexahydroterephthalate, N,N'-bis(1-oxyl-2,2,6,6-tetramethylpiperidin-4-yl) adipamide, 2,4,6-tris-[N-butyl-N-(1-oxyl-2,2,6,6-tetramethylpiperidin-4-yl)]-s-triazine, 2,4,6-tris-[N-(1-oxyl-2,2,6,6-tetramethylpiperidin-4-yl)]-s-triazine, 4,4'-ethylenebis(1-oxyl-2,2,6,6-tetramethylpiperazin-3-one), and mixtures thereof (See, for example, U.S. Pat. No. 9,266,797.) Any of these compounds can be present at very low amounts (less than 50 ppm, 25 ppm, 10 ppm, etc., as described herein) in a polymerizable monomer composition, or can be excluded from the composition altogether.

The nitrogen- and oxygen-containing aromatic antipolymerant can be present in a composition with a solvent, or a combination of solvents. A solvent or solvent combination can be chosen so that one or more of the nitrogen- and oxygen-containing aromatic antipolymerant is soluble in the solvent or solvent combination. If the nitrogen- and oxygen-containing aromatic antipolymerant is a liquid at ambient conditions, a miscible solvent can be chosen.

Useful solvents include any solvent in which the nitrogen- and oxygen-containing aromatic antipolymerant is soluble or can be stably suspended. In some embodiments, a solvent or solvent combination can be selected from water soluble or water miscible solvents such glycol-based solvents and hydrophobic or hydrocarbon solvents such as aromatic solvents, paraffinic solvents, or mixtures of both.

Exemplary glycol solvents include, but are not limited to, $C_1$-$C_8$ glycols such as ethylene glycol, propylene glycol, diethylene glycol, and triethylene glycol, ethers of such glycols such as di ethylene glycol monobutyl ether, diethylene glycol monomethyl ether, diethylene glycol monoethyl ether, diethylene glycol monobutyl ether, triethylene glycol, triethylene glycol monomethyl ether, liquid polyethylene glycol, dipropylene glycol, dipropylene glycol monomethyl ether, dipropylene glycol monoethyl ether, and a low molecular weight polypropylene glycol and the like and combinations thereof. Commercial solvents such as Butyl Carbitol and Butyl CELLOSOLVE™, which contains primarily Butyl CARBITOL™, which consists primarily of ethylene glycol monobutyl ether may be used and are available from DOW.

Other exemplary hydrophobic or hydrocarbon solvents include heavy aromatic naphtha, toluene, ethylbenzene, isomeric hexanes, benzene, xylene, such as ortho-xylene, para-xylene, or meta-xylene, and mixtures of two or more thereof.

In some embodiments, the solvent is selected from glycol and aromatic naphta and combinations thereof.

The amount of nitrogen- and oxygen-containing aromatic antipolymerant (with one or more optional components), in a solvent, or a combination of solvents, can be described one or more ways, such as by the percent solids (wt) of the component(s) in the composition, or by the molar amount of solid components in the composition.

As an example, a stock composition of nitrogen- and oxygen-containing aromatic antipolymerant can be dissolved in a solvent to a concentration of about at least about 0.00001% (wt), at least about 5% (wt), such as in an amount in the range from about 0.00001% (wt) to about 50% (wt).

An amount of the stock composition including nitrogen- and oxygen-containing aromatic antipolymerant can be added to a monomer-containing composition or composition capable of forming monomer, to provide the antipolymerant at a concentration effective to inhibit polymerization of monomer.

The polymerizable monomer that is subjected to polymerization inhibition by the nitrogen- and oxygen-containing aromatic can include a vinyl or ethylenically unsaturated group. For example, the components of the nitrogen- and oxygen-containing aromatic antipolymerant and any optional component can be added to a composition that includes one or more of the following polymerizable monomers: acrolein, acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyl acetate, vinyltoluene, and vinylpyridine.

The polymerizable monomer can be present in a crude mixture of compounds, a semi-refined mixture of compounds, or a fully-refined mixture of compounds. For example, the nitrogen- and oxygen-containing aromatic antipolymerant can be added to a process stream that includes the polymerizable monomer and one or more other components that are different than the polymerizable monomer. In methods, the nitrogen- and oxygen-containing aromatic antipolymerant can be added before, during, or after, (or combinations thereof) a processing step, such as distillation, wherein compounds in the composition are separated from one another. The nitrogen- and oxygen-containing aromatic antipolymerant can inhibit polymerization of monomer at any one or more stages in a processing system, and therefore reduce or prevent fouling of equipment.

Alternatively, the nitrogen- and oxygen-containing aromatic antipolymerant can be added to a process stream that includes a compound capable of forming into a polymerizable monomer a monomer precursor), such as ethylbenzene which is a precursor to styrene. For example, in embodiments, a composition may include a compound that is capable of forming a polymerizable monomer as an unwanted by-product. In this situation, the presence of the nitrogen- and oxygen-containing aromatic antipolymerant can inhibit polymerization of the monomer if it does form as a by-product, and can therefore reduce or prevent fouling of equipment.

In modes of practice, the nitrogen- and oxygen-containing aromatic antipolymerant is introduced into a monomer-containing composition or a composition that includes a compound capable of forming a polymerizable monomer, at a desired concentration effective to inhibit monomer polymerization. The nitrogen- and oxygen-containing aromatic antipolymerant can be added to a composition that includes one or more polymerizable monomers, or one or more compounds that are capable of forming polymerizable monomers. The monomer(s) and/or monomer-forming compound(s) can be present at any concentration in the composition, such as in very small amounts (ppm) or amounts wherein the monomer(s) and/or monomer-forming compound(s) are present in bulk amounts in the composition (e.g., 50% (wt) or greater). Exemplary ranges are from any one of about 5 ppm, about 20 ppm, about 50 ppm, or about 100 ppm (0.1%) to , about 10% (wt), about 25% (wt), about 50% (wt), or about 75% (wt). In some modes of practice, at a polymerizable monomer concentration in the range of about 50 to about 200 ppm.

The amount of nitrogen- and oxygen-containing aromatic antipolymerant in a composition that includes monomer(s) and/or monomer-forming compound(s) can be chosen based on the monomer/compound type, the amount of monomer/compound in the composition, the type of composition having the monomer/compound, any processing, treatment, or storage conditions for the composition, and the presence of any one or more optional compounds that are different than the nitrogen- and oxygen-containing aromatic antipolymerant and that are added to the composition. The nitrogen- and oxygen-containing aromatic antipolymerant can be added to the composition in an amount to provide a desired level of polymerization inhibition.

In embodiments, the nitrogen- and oxygen-containing aromatic antipolymerant can be used in an amount of at least about 0.10 ppm, such as in the range of about 0.10 ppm to about 50,000 ppm, in the range of about 0.10 ppm to about 25,000 ppm, about 0.10 ppm to about 10,000 ppm, about 25 ppm to about 5,000 ppm, about 25 ppm to about 2,500 ppm, about 50 ppm to about 1,000 ppm, about 50 ppm to about 1,000 ppm, about 75 to about 500 ppm, about 100 to 300 ppm, about 125 to about 275 ppm, or about 150 to about 250 ppm.

In some modes of practice the nitrogen- and oxygen-containing aromatic antipolymerant is used before or after a polymerizable monomer-containing composition is treated with a polymerization inhibitor that is different than the nitrogen- and oxygen-containing aromatic, such as a nitroxide-containing polymerization inhibitor (e.g., HTEMPO, etc.). In some modes of practice, the nitrogen- and oxygen-containing aromatic antipolymerant is added to a polymerizable monomer composition after the composition has been treated with a nitroxide-containing polymerization inhibitor, and the inhibitor has been at least substantially consumed or has otherwise at least lost most of its inhibitor activity. For example, a nitroxide-containing polymerization inhibitor can be added to a monomer-containing composition at a first time point and then the composition can be monitored to determine any increase in the formation of polymer and/or presence of inhibitor, and if there is an increase in formation of polymer or reduction in inhibitor, the nitrogen- and oxygen-containing aromatic antipolymerant can be added at a second time point to maintain inhibition of polymerization.

In other modes of practice, the nitrogen- and oxygen-containing aromatic antipolymerant can be added to a monomer-containing composition at a first time point, and then one or more other compounds useful for inhibiting polymerization that is different than the nitrogen- and oxygen-containing aromatic can be added to the composition at one or more later time point(s) (e.g., second, third, etc.).

The nitrogen- and oxygen-containing aromatic antipolymerant can be added to a polymerizable monomer composition in any one or more different ways, such as addition of the antipolymerant in single dose, continuous addition, semi-continuous addition, intermittent addition, or any combination of these methods. In a continuous addition, the nitrogen- and oxygen-containing aromatic antipolymerant can be added at a constant or variable rate. The mode or modes of addition of the nitrogen- and oxygen-containing aromatic antipolymerant can be chosen based on the polymerizable monomer-containing composition and how it is being stored, processed, or otherwise treated. For example, in a process stream involving the movement and separation of polymerizable monomer, or a compound that can form a polymerizable monomer, from other components such as a distillation apparatus, the nitrogen- and oxygen-containing aromatic antipolymerant can be added in a continuous or semi-continuous manner to account for new monomer or monomer precursor constantly being introduced.

The term "fouling" refers to the formation of polymers, prepolymers, oligomer and/or other materials which would become insoluble in and/or precipitate from a stream and deposit on equipment under conditions of operating the equipment. In turn, the nitrogen- and oxygen-containing aromatic antipolymerant can be referred to as an "antifoulant" as it prevents or reduces such formation.

Optionally, the ability of the compositions of the disclosure to inhibit polymerization can be described relative to a composition that does not include the nitrogen- and oxygen-containing aromatic antipolymerant, or that includes a comparative compound. The effect of the nitrogen- and oxygen-containing aromatic antipolymerant can be understood by measuring the formation of a polymer (e.g., polystyrene) in a monomer (e.g., styrene) composition over time, in the presence of a composition that includes the nitrogen- and oxygen-containing aromatic antipolymerant as compared to one that does not include the nitrogen- and oxygen-containing aromatic antipolymerant, or that uses an antipolymerant having chemistry that is different than one of the disclosure. The advantageous antipolymerant effect of various nitrogen- and oxygen-containing aromatic compounds is exemplified with reference to the Examples of this disclosure and data shown in Tables 1 and 2 (e.g., regarding the antipolymerant effects of N,N-bis(2-hydroxy-2-phenylethyl]-p-aminophenol (BHPEAP), N,N-bis[3-(2-ethylbutoxy)-2-hydroxypropyl]-p-aminophenol (BBHPAP), and N,N-bis-(3-butoxy-2-hydroxypropyl)-p-aminophenol (BBHPAP)). In these examples, solutions of styrene and antipolymerant were prepared. Polymerizations were allowed to proceed at 120° C., and every 20 minutes for up to two hours, samples were removed from the heat and the reaction was quenched by placing the samples on ice. Polymer concentration was measured and reported as percent weight.

For example, a composition of the disclosure with a nitrogen- and oxygen-containing aromatic antipolymerant can inhibit polymerization of monomer by more than 50%, by more than 60%, by more than 70%, by more than 80%, by more than 85%, by more than 90%, by more than 92.5%, by more than 95%, or by more than 97%, as compared to a composition with a non-nitrogen- and oxygen-containing aromatic (e.g., a di-butyl-1,4-benzoquinone), under the same conditions.

The nitrogen- and oxygen-containing aromatic antipolymerant can be used in conjunction with compositions containing polymerizable monomers and "process equipment" such as reactors, reactor beds, pipes, valves, distillation columns, trays, condensers, heat exchangers, compressors, fans, impellers, pumps, recirculators, inter-coolers, sensors, and the like, that are associated with the process and which may be subject to fouling by monomer polymerization. This term also includes sets of these components where more than one of the components is part of a "system."

In one preferred method of use, a composition of the disclosure with nitrogen- and oxygen-containing aromatic antipolymerant and solvent (e.g., glycol) is used with a process that involves a distillation tower that is used to separate and purify vinylic monomers, such as styrene. For example, in art-known processes ethylbenzene can be subjected to a catalytic dehydrogenation reaction which results in the formation of styrene. The reaction product containing styrene also contains other compounds such as aromatics like toluene and benzene, unreacted ethylbenzene, and other materials such as polymers. This mixture of compounds is generally fractionally distilled using one or more distillations towers. Typically, heat is used to help separate the components in the distillation tower. Following distillation the fractionated components can be separated into pure product streams with higher purity. Optionally, the nitrogen- and oxygen-containing aromatic antipolymerant is used along with one or more secondary components such as stabilizers like butylated hydroxytoluene (BHT) and tert-butylcatechol (TBC). In an exemplary mode of practice these components are used in a distillation tower that is used to separate and purify vinylic monomers.

The nitrogen- and oxygen-containing aromatic antipolymerant-containing composition can be introduced into a stream leading from the reaction bed to the distillation tower, or can be directly added to the distillation tower. The compositions can be added prior to heating the monomer composition or while heating the monomer composition in the distillation tower. In embodiments, the nitrogen- and oxygen-containing aromatic antipolymerant compound has a boiling point that is higher than that of the desired compound or distillate (e.g., a monomer such as styrene) subject to distillation tower and during the distillation process the desired compound is separated from the nitrogen- and oxygen-containing aromatic antipolymerant compound by virtue of temperature difference. In embodiments, the boiling point difference between the compound of interest and the nitrogen- and oxygen-containing aromatic antipolymerant is about 10° C. or greater, about 15° C. or greater, about 20° C. or greater, about 25° C. or greater, about 30° C. or greater, about 35° C., or greater, about 40° C. or greater, about 45° C. or greater, or about 50° C. or greater.

Alternatively, or in addition to adding the nitrogen- and oxygen-containing aromatic antipolymerant during a distillation process, the composition can be optionally or further added to a distillation effluent stream, such as a purified styrene stream. Optionally, another antipolymerant can be added to a distillation effluent stream prior to or along with the nitrogen- and oxygen-containing aromatic antipolymerant.

The nitrogen- and oxygen-containing aromatic antipolymerant, optionally used in combination with one or more other components, can be used with any "hydrocarbon process stream" which can include unsaturated monomer in order to stabilize the stream during transportation and storage. In some modes of practice, the nitrogen- and oxygen-containing aromatic antipolymerant can be used in conjunction with a "petroleum product" which refers to any hydrocarbon product obtained from a subterranean reservoir, any product derived therefrom, or any mixture thereof. Polymerizable monomers are found in or can be chemically derived from petroleum products. Nonlimiting examples of petroleum products include but are not limited to crude oil, reduced crude oil, crude distillate, heavy oil, or bitumen, hydrotreated refined oil, byproducts of petroleum product processing such as pyrolysis, hydrotreating, or phase separation, or mixtures of two or more of these. A liquid petroleum product is a petroleum product that is substantially a liquid at 20° C.

The nitrogen- and oxygen-containing aromatic antipolymerant can be added to or can be present in a "petroleum process stream" which refers to any petroleum product disposed within petroleum process equipment in fluid contact with an interior surface thereof.

The petroleum process stream can include, or can be capable of forming as a by-product, one or more polymerizable monomer. The process stream may be substantially static, such as a petroleum product disposed within in a settler (separator) or storage container for a selected period of contact, such as up to two years. The process stream may be substantially dynamic, such as a liquid petroleum product disposed within a pipe during transportation of the product from a first location to a second location. In some embodiments the process stream includes one or more additional components related to petroleum processing; such components are not particularly limited.

"Petroleum process equipment" or "petroleum process apparatus" refers to a man-made item having an interior surface including a metal, further wherein one or more petroleum products are fluidly contacted with the metal for any period of time and at any temperature further as determined by context. Petroleum process equipment includes items for removing petroleum products from a subterranean reservoir, for transporting one or more petroleum products from a first location to a second location, or for separating, refining, treating, isolating, distilling, reacting, metering, heating, cooling, or containing one or more petroleum products.

In embodiments, compositions including the nitrogen- and oxygen-containing aromatic antipolymerant are thermally stable and have antipolymerant activity in processing streams or other polymerizable monomer-containing compositions at temperatures of about 20° C. to about 400° C., for example about 100° C. to 400° C., or about 100° C. to 350° C., or about 100° C. to 300° C., or about 100° C. to 250° C., or about 100° C. to 200° C., or about 100° C. to 150° C.

In embodiments, compositions including nitrogen- and oxygen-containing aromatic antipolymerant can be introduced into a composition with a polymerizable monomer, such as a liquid petroleum process stream in a batch-wise, a continuous, or a semi-continuous manner. In some embodiments, the nitrogen- and oxygen-containing aromatic antipolymerant (and any other optional component) are introduced manually; and in other embodiments, their introduction is automated. In embodiments, the amount of the nitrogen- and oxygen-containing aromatic antipolymerant introduced over a selected unit of time is varied with a variable composition of the associated process stream. Such variability in dosing may be conducted manually by periodic testing of the process equipment interior surfaces, following by adjusting the amount of the composition up or down based on test results; or automatically by monitoring of one or more conditions within the interior of the petroleum process equipment and signaling the need to apply more composition to the process stream.

In some embodiments, the nitrogen- and oxygen-containing aromatic antipolymerant is added to a petroleum product that is a crude oil, a reduced crude oil, a heavy oil, a bitumen, a coker charge, a hydrotreater influent, a hydrotreater effluent, a flashed crude, a light cycle oil, or a diesel or naphtha refinery stream. In embodiments, the antipolymerant is added to petroleum process equipment conventionally associated with the collecting, processing, transportation, or storage of one or more of crude oil, reduced crude oil, crude distillate, heavy oil, bitumen, coker charge, flashed crude, light cycle oil, or a diesel or naphtha refinery stream, including pipes and associated infrastructure used to fluidly connect process equipment items together to facilitate processing of a process stream disposed therein.

Equipment containing the polymerizable monomer-containing compositions that are treated with the nitrogen- and oxygen-containing aromatic antipolymerant and any other optional component can result in reduction or elimination of fouling interior surface of the equipment. In embodiments, fouling is measured as a relative increase in retention of solids within the treated composition compared to the retention of solids in untreated composition over the same time period. In embodiments, fouling is measured as a relative decrease in the weight or volume of precipitate arising from a selected period of contact of a treated process stream in an associated process equipment item, relative to the same period of contact of the process equipment with the corresponding untreated process stream. Stated differently, a reduction in fouling is a relative decrease in the measured weight or volume of solids deposited on or precipitated from process equipment contacted with the treated process stream over a selected period of time, when compared to the weight or volume of solids deposited or precipitated from an untreated process stream over the same period of time.

The nitrogen- and oxygen-containing aromatic antipolymerant can also inhibit unwanted polymerization and fouling of the process equipment in a primary fractionation process, light ends fractionation, non-aromatic halogenated vinyl fractionation and stabilization, process-gas compression, dilution steam system, caustic tower, quench water tower, quench water separator (pyrolysis gasoline), butadiene extraction, propane dehydrogenation, diesel and petrol fuel stabilization, olefin metathesis, styrene purification, hydroxy hydrocarbon purification, stabilization of vinylic monomers during transportation and storage, or delays the polymerization of resins and compositions comprising ethylenicaily unsaturated species.

The nitrogen- and oxygen-containing aromatic antipolymerant can be added at any given point in a process and at one or more locations. For example, an antipolymerant composition can be added directly at the interstage coolers or compressors or upstream of the inter-coolers or compressors. The nitrogen- and oxygen-containing aromatic antipolymerant can be added continuously or intermittently, to the process equipment as required preventing or reducing fouling.

The nitrogen- and oxygen-containing aromatic antipolymerant can be introduced to desired systems by any suitable method. For example it may be added in neat or a dilute solution. In some embodiments, a composition containing the nitrogen- and oxygen-containing aromatic antipolymerant can be applied as a solution, emulsion, or dispersion that is sprayed, dripped, poured or injected into a desired opening within a system or onto the process equipment or process condensate. In some embodiments, the composition may be added with a washoil or an attemperation water.

After introducing the composition to process equipment, treated process equipment can be observed to have less deposition on equipment than in process equipment without addition of the composition. Reduction or prevention in fouling can be evaluated by any known method or test. In some embodiments, the reduction or prevention of fouling can be accessed by measuring the time it takes for a sample with and without the antifoulant composition to gel.

EXAMPLE 1: SYNTHESIS OF N,N-Bis-(2-Hydroxy-2-Phenyethyl)-p-Aminophenol

The following were charged into a three-neck, 1 L round-bottomed flask with; a magnetic follower, 45.396 g (815.3 mmol) styrene oxide, 45.396 g (407.7 mmol) p-aminophenol and 142.804 g of toluene. Two stoppers and a condenser were fitted to the flask. The flask was placed on a heating block followed by the reflux of the reaction mixture under agitation for six hours. Following the completion of the reaction, the solvent was removed to yield a viscous gum. The product was characterized for purity and the confirmation of the structure.

EXAMPLE 2: N,N-Bis-(3-Butoxy-2-Hydroxypropyl)-p-Aminophenol

The procedure in Example 1 was used to synthesize N,N-bis-(3-butoxy-2-hydroxypropyl)-p-aminophenol using 14.483 g (132.7 mmol)p-aminophenol, 36.375 g (265.4 mmol) of n-butyl glycidyl ether, In lieu of toluene, butyl glycol was used as a solvent.

EXAMPLE 3: QMPh ANTIPOLYMERANT (COMPARATIVE)

A styrene solution with a QMPh concentration of 0.679 mmolal was prepared. An inhibitor removal column was used to remove the 4-tert-butylcatechol (TBC) stabilizer in the styrene. The solutions were partitioned into twenty-four threaded pressure tubes. Dissolved oxygen removed from the solutions using nitrogen. To prevent the evaporation of the styrene, each tube was capped with PTFE screw caps. Each of the caps had a fluoroelastomer (FETFE) O-ring. After capping all the tubes, polymerization was performed by the loading the tubes into a heating block that had been preheated to 12° C. Every 20 minutes, four tubes were taken from the block. The total polymerization time was 2 hours. A bath of water with crushed ice was used to quench the polymerization reaction. Following the dilution of the cooled polymer solutions using toluene, the polymer concentration was measured and reported as percent weight. See Table 1.

EXAMPLE 4: DNBP ANTIPOLYMERANT (COMPARATIVE)

A composition comprising 0.679 mmolal of DNBP and stabilizer-free styrene was prepared. Following the procedure in Example 3, the partitioned solutions were polymerized, and the polymer concentrations measured accordingly. See Table 1.

EXAMPLE 5: N,N-Bis[3-(2-ethylbutoxy)-2-hydroxypropyl]-p-aminophenol

A solution consisting of 0.679 mmolal of N,N-bis[3-(2-ethylbutoxy)-2-hydroxypropyl]-p-aminophenol (BEBH-PAP) and stabilizer-free styrene was prepared according to the method in Example 3. Polymerization reactions and the determination of the polymer concentrations were carried out as per the protocol in Example 3 as well. See Table 1.

EXAMPLE 6: N,N-Bis-(2-Hydroxy-2-Phenyethyl)-p-Aminophenol

A styrene solution containing of 0.679 mmolal of N,N-bis-(2-hydroxy-2-phenyethyl)-p-aminophenol (BHPEAP) was prepared using stabilizer-free styrene. In accordance with the method in Example 3, polymerization reactions and the determination of the polymer concentrations were performed. See Table 1.

EXAMPLE 7: N,N-Bis-(3-Butoxy-2-Hydroxypropyl) p-Aminophenol

Using the procedure in Example 3, the antipolymerant activity of N,N-bis-(3-butoxy-2-hydroxypropyl)-p-aminophenol (BBHPAP) was tested using a stabilizer-free solution of styrene in which the concentration of this architecture was 0.679 mmolal. See Table 1.

EXAMPLE 8: UNTREATED STYRENE

Immediately after removing TBC from styrene, 10-mL aliquots of said styrene were charged into each of the afore-mentioned pressure tubes. After the dissolved oxygen was purged out of the solutions, polymerizations reactions and polymer analysis were conducted in accordance with the procedure in Example 1,

TABLE 1

| Time | 0.679 mmolal QMPh | 0.679 mmolal DNBP | 0.679 mmolal BEBHPAP | 0.679 mmolal BHPEAP | 0.679 mmolal BBHPAP |
| --- | --- | --- | --- | --- | --- |
| 0 | 0 | 0 | 0 | 0 | 0 |
| 20 | 0.226 | 0.0290 | 0.0377 | 0.0174 | 0.0210 |
| 40 | 0.436 | 0.0599 | 0.0398 | 0.0196 | 0.0240 |
| 60 | 0.792 | 0.144 | 0.0456 | 0.0254 | 0.0306 |
| 80 | 0.949 | 0.396 | 0.0464 | 0.0324 | 0.0326 |
| 100 | 1.48 | 0.567 | 0.0510 | 0.0362 | 0.0399 |
| 120 | 2.03 | 0.832 | 0.0552 | 0.0418 | 0.0440 |

EXAMPLE 9: N,N-bis(2-Hydroxy-2-Phenylethy]-p-Aminophenol ANTIPOLYMERANT

A solution consisting of 0.33 mmolal of N,N-bis(2-hydroxy-2-phenylethyl]-p-aminophenol (BHPEAP) and stabilizer-free styrene was prepared according to the method in Example 3. However, the solution was used without the removal of dissolved oxygen. Polymerization reactions and the determination of the polymer concentrations were carried out as per the protocol in Example 3 as well. See Table 2.

EXAMPLE 10: QMPh ANTIPOLYMERANT (COMPARATIVE)

A composition comprising 0.33 mmolal of QMPh (Phenyl Quinone Methide) and stabilizer-free styrene was prepared. As in Examples 8, the solution was used without the removal of dissolved oxygen. Thereafter, following the procedure in Example 3, the partitioned solutions were polymerized, and the polymer concentrations measured accordingly. See Table 2.

EXAMPLE 11: DNBP ANTIPOLYMERANT (COMPARATIVE)

A composition comprising 0.33 mmolal of DNBP and stabilizer-free styrene was prepared. Following the procedure in Example 8, the partitioned solutions were polymerized, and the polymer concentrations measured accordingly. See Table 2.

TABLE 2

| Time (minutes) | 0.33 mmol. BHPEAP | 0.33 mmol. QMPh | 0.33 mmol. DNBP |
| --- | --- | --- | --- |
| 0 | 0 | 0 | 0 |
| 20 | 0.0191 | 0.625 | 0.0725 |
| 40 | 0.0367 | 2.95 | 0.959 |
| 60 | 0.0738 | 6.97 | 4.59 |
| 80 | 2.38 | 10.3 | 7.46 |
| 100 | 6.40 | 14.4 | 10.9 |
| 120 | 9.29 | 18.2 | 14.2 |

Results are also illustrated in the FIGURE.

What is claimed is:

1. A method for inhibiting the polymerization of monomers in a monomer-containing composition, the method comprising:

adding a nitrogen- and oxygen-containing aromatic antipolymerant to a composition comprising a polymerizable monomer, wherein the polymerizable monomer is
   (a) selected from the group consisting of acrolein, acrylonitrile, alkylated styrene, chloroprene, divinylbenzene, ethyl acrylate, ethyl methacrylate, isoprene, methyl methacrylate, methyl acrylate, α-methylstyrene, methacrylonitrile, styrene, styrene sulfonic acid, vinyl acetate, vinyltoluene, and vinylpyridine, (b) selected from the group consisting of ethylene, acetylene, methylacetylene, vinylacetylene, propylene, butene, butyne, and butadiene;

or (c) an unsaturated cyclic aliphatic compound, the nitrogen- and oxygen-containing aromatic antipolymerant being a compound of Formula I:

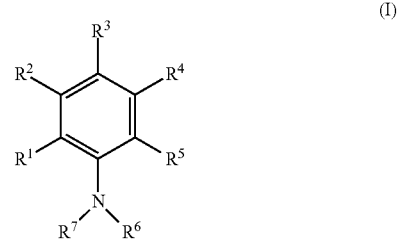

(I)

wherein at least one of —$R^1$, —$R^2$, —$R^3$, —$R^4$, and —$R^5$ is or are —$OR^8$, wherein $R^8$ is selected from the group consisting of —H, alkyl, aryl, alkyl-aryl, and aryl-alkyl having 3-18 carbon atoms, wherein any one or more of —$R^1$, —$R^2$, —$R^3$, —$R^4$, and —$R^5$ that is not —$OR^8$ is or are selected from the group consisting of hydrogen, alkyl, aryl, alkyl aryl and aryl alkyl, or any two adjacent groups of —$R^1$, —$R^2$, —$R^3$, —$R^4$, and —$R^5$ that are not —$OR^8$ form one or more ring structures;

wherein $R^6$ and $R^7$ are, independently, carbon-containing groups, and at least one of $R^6$ and $R^7$ comprises one or more oxygen atom(s) separated from the N atom by one or more carbon atoms;

wherein the compound of Formula I inhibits polymerization of the polymerizable monomer in the composition.

2. The method of claim 1 wherein the one or more oxygen atom(s) is or are present in the form of a hydroxyl group, an ether group, or both.

3. The method of claim 1 wherein the one or more oxygen atom(s) is or are separated from the N atom by two or more carbon atoms.

4. The method of claim 1, wherein one or both of $R^6$ and $R^7$ is or are of the formula: —$R^9OR^{10}$, wherein $R^9$ is a hydrocarbylene group, optionally substituted, and $R^{10}$ is a hydrocarbyl group, optionally substituted, wherein one or both of $R^9$ and $R^{10}$ optionally have an amount of carbon atoms in the range of 1-12, 1-8, 1-6, or 1-3.

5. The method of claim 4 wherein $R^9$ is selected from the group consisting of methylene, ethylene, propylene, isopropylene, butylene, isobutylene, sec-butylene, tert-butylene, pentylene, and hexylene.

6. The method of claim 4 wherein $R^{10}$ is selected from the group consisting of linear alkyl, branched alkyl, cyclic alkyl, aryl, alkyl-aryl, and aryl-alkyl, each having 1-18 carbon atoms, wherein $R^{10}$ is optionally:
   methyl,
   ethyl,
   propyl, isopropyl, butyl, isobutyl, sec-butyl, tert-butyl,
pentyl, cyclopentyl, isopentyl, neopentyl,
hexyl, cyclohexyl, 1-, 2-, or 3-methylbutyl, 1,1-, 1,2-, or 2,2-dimethylpropyl, 1-ethyl-propyl, 1-, 2-, 3-, or 4-methylpentyl, 1,1-, 1,2-, 1,3-, 2,2-, 2,3-, or 3,3-dimethylbutyl, 1- or 2-ethylbutyl, 1-ethyl-1-methylpropyl, 1,1,2- or 1,2,2-trimethylpropyl, methylcyclopentyl;
heptyl, 2-methylhexyl, 3-methylhexyl, 4-methylhexyl, 5-methylhexyl, 3-ethylpentyl, 2,2,3-trimethylbutyl, 2,2-dimethylpentyl, 2,3-dimethylpentyl, 2,4-dimethylpentyl, 3,3-dimethylpentyl, 3,4-dimethylpentyl, 4,4-dimethylpentyl, cycloheptyl, 1-methylcyclohexyl, 2-methylcyclohexyl;
octyl, 2-methylheptyl, 3-methylheptyl, 4-methylheptyl, 2-ethylhexyl, 3-ethylhexyl, 4-ethylhexyl, 5-ethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethyl-2-methylpentyl, 3-ethyl-3-methylpentyl, 2,2,3-trimethylpentyl, 2,2,4-trimethylpentyl, 2,3,3-trimethylpentyl, 2,3,4-trimethylpentyl, or 2,2,3,3-tetramethylbutyl.

7. The method of claim 4 wherein the nitrogen- and oxygen-containing aromatic antipolymerant is a compound selected from the group consisting of:
4-bis[(methoxymethyl)amino]phenol, 4-bis[(2-methoxyethyl)amino]phenol, 4-bis[(3-methoxypropyl)amino]phenol, 4-bis[(4-methoxybutyl)amino]phenol, 4-bis[(5-methoxypentyl)amino]phenol, 4-bis[(6-methoxyhexyl)amino]phenol, 4-bis[(methoxyphenyl)amino]phenol;
4-bis[(ethoxymethyl)amino]phenol, 4-bis[(2-ethoxyethyl)amino]phenol, 4-bis[(3-ethoxypropyl)amino]phenol, 4-bis[(4-ethoxybutyl)amino]phenol, 4-bis[(5-ethoxypentyl)amino]phenol, 4-bis[(6-ethoxyhexyl)amino]phenol, 4-bis[(ethoxyphenyl)amino]phenol;
4-bis[(propoxymethyl)amino]phenol, 4-bis[(2-propoxyethyl)amino]phenol, 4-bis[(3-propoxypropyl)amino]phenol, 4-bis[(4-propoxybutyl)amino]phenol, 4-bis[(5-propoxypentyl)amino]phenol, 4-bis[(6-propoxyhexyl)amino]phenol, 4-bis[(propoxyphenyl)amino]phenol;
4-bis[(butoxymethyl)amino]phenol, 4-bis[(2-butoxyethyl)amino]phenol, 4-bis[(3-butoxypropyl)amino]phenol, 4-bis[(4-butoxybutyl)amino]phenol, 4-bis[(5-butoxypentyl)amino]phenol, 4-bis[(6-butoxyhexyl)amino]phenol, and 4-bis[(butoxyphenyl)amino]phenol.

8. The method of claim 4, wherein $R^9$ is a hydroxylated hydrocarbylene group, wherein $R^9$ is optionally selected from the group consisting of:

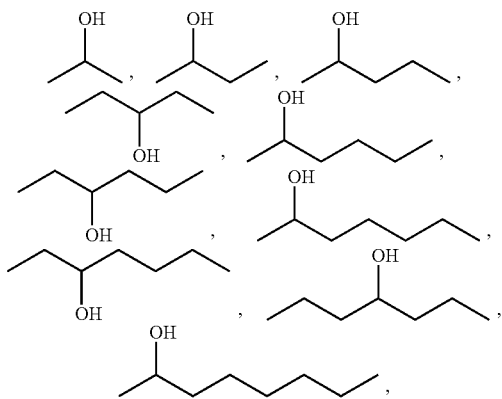
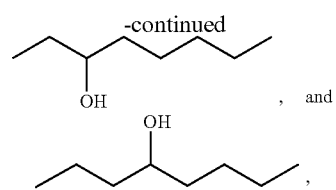

or $—R^9OR^{10}$ is selected from the group consisting of:

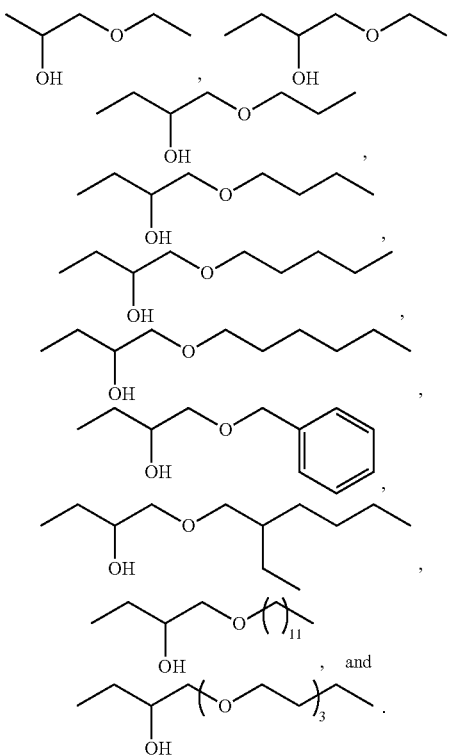

9. The method of claim 8 wherein the nitrogen- and oxygen-containing aromatic antipolymerant is a compound selected from the group consisting of
4-bis[(2-methoxy-1-hydroxy-ethyl)amino]phenol, 4-bis[(3-methoxy-2-hydroxy-propyl)amino]phenol, 4-bis[(4-methoxy-2-hydroxy-butyl)amino]phenol, 4-bis[(5-methoxy-2-hydroxy-pentyl)amino]phenol, 4-bis[(6-methoxy-2-hydroxy-hexyl)amino]phenol, 4-bis[(methoxyhydroxyphenyl)amino]phenol;
4-bis[(2-ethoxy-1-hydroxy-ethyl)amino]phenol, 4-bis[(3-ethoxy-2-hydroxy-propyl)amino]phenol, 4-bis[(4-ethoxy-2-hydroxy-butyl)amino]phenol, 4-bis[(5-ethoxy-2-hydroxy-pentyl)amino]phenol, 4-bis[(6-ethoxy-2-hydroxy-hexyl)amino]phenol, 4-bis[(ethoxyhydroxyphenyl)amino]phenol;
4-bis[(2-propoxy-1-hydroxy-ethyl)amino]phenol, 4-bis[(3-propoxy-2-hydroxy-propyl)amino]phenol, 4-bis[(4-propoxy-2-hydroxy-butyl)amino]phenol, 4-bis[(5-propoxy-2-hydroxy-pentyl)amino]phenol, 4-bis[(6-propoxy-2-hydroxy-hexyl)amino]phenol, 4-bis[(propoxyhydroxyphenyl)amino]phenol,
4-bis[(2-butoxy-1-hydroxy-ethyl)amino]phenol, 4-bis[(3-butoxy-2-hydroxy-propyl)amino]phenol, 4-bis[(4-butoxy-2-hydroxy-butyl)amino]phenol, 4-bis[(5-butoxy-2-hydroxy-pentyl)amino]phenol, 4-bis[(6-butoxy-2- hydroxy-hexyl)amino]phenol, and 4-bis[(butoxyhydroxyphenyl)amino]phenol.

10. The method of claim 1 wherein both of $R^6$ and $R^7$ are hydroxylated hydrocarbyl groups, wherein the hydroxylated hydrocarbyl groups have an amount of carbon atoms in the range of 1-18, 1-12, 1-8, 1-6, or 1-3.

11. The method of claim 10 wherein the hydroxylated hydrocarbyl groups are selected from linear alkanol, branched alkanol, cyclic alkanol, hydroxylated aryl, hydroxylated alkyl-aryl, and hydroxylated aryl-alkyl.

12. The method of claim 11 wherein the hydroxylated hydrocarbyl formula $-(CR^{24}R^{25})_q(CHOH)(CH_2)_zR^{11}$, wherein $R^{24}$ and $R^{25}$ are independently selected from H, $R^{10}$, and $OR^{10}$), wherein q and z are independently integer in the range of 1-12, optionally integers in the range of 1-6 or 1-3, and wherein $R^{11}$ is selected from the group consisting of $R^{10}$, and

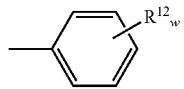

wherein $R^{12}$ is independently selected from the group consisting of H and $R^{10}$ and wherein w is an integer in the range of 1-5,
wherein $R^{10}$ is hydrocarbyl group, optionally substituted, wherein $R^{10}$ optionally has an amount of carbon atoms in the range of 1-12, 1-8, 1-6, or 1-3.

13. The method of claim 12 wherein the nitrogen- and oxygen-containing aromatic antipolymerant is a compound selected from the group consisting of
4-bis[(1-hydroxyethyl)amino]phenol,
4-bis[(1-hydroxypropyl)amino]phenol, 4-bis[(2-hydroxypropyl)amino] phenol,
4-bis[(1-hydroxybutyl)amino]phenol, 4-bis[(2-hydroxybutyl)amino]phenol, 4-bis[(3-hydroxybutyl)amino] phenol,
4-bis[(1-hydroxypentyl)amino]phenol, 4-bis[(2-hydroxypentyl)amino] phenol, 4-bis[(3-hydroxypentyl)amino] phenol, 4-bis[(4-hydroxypentyl)amino] phenol, 4-bis[(1-hydroxyhexyl)amino]phenol, 4-bis[(2-hydroxyhexyl)amino]phenol,
4-bis[(3-hydroxyhexyl)amino]phenol, 4-bis[(4-hydroxyhexyl)amino]phenol, 4-bis[(5-hydroxyhexyl)amino]phenol,4-bis[(2-hydroxy-2-phenylethyl)amino]phenol, 4-bis[(2-hydroxy-3-phenylpropyl)amino]phenol, 4-bis[(3-hydroxy-3-phenylpropyl)amino]phenol, 4-bis[(2-hydroxy-4-phenylbutyl)amino]phenol, 4-bis[(3-hydroxy-4-phenylbutyl)amino]phenol, and 4-bis[(4-hydroxy-4-phenylbutyl)amino]phenol.

14. The method of claim 1 wherein either
(I) $R^6$ and $R^7$ are, independently, carbon-containing groups comprising one or more oxygen atom(s) separated from the N atom by one or more carbon atoms; or
(II) one or both of $R^6$ and $R^7$ are of the formula: $-R^9OR^{10}$, wherein $R^9$ is a hydrocarbylene group, optionally substituted, and $R^{10}$ is a hydrocarbyl group, optionally substituted, wherein one or both of $R^9$ and $R^{10}$ optionally have an amount of carbon atoms in the range of 1-12, 1-8, 1-6, or 1-3.

15. The method of claim 1 wherein the nitrogen- and oxygen-containing aromatic antipolymerant is a compound selected from the group consisting of 4-bis[(hydroxymethyl)amino]phenol, 4-bis[(2-hydroxyethyl)amino]phenol, 4-bis[(3-hydroxypropyl)amino]phenol, 4-bis[(4-hydroxybutyl)amino]phenol, 4-bis[(5-hydroxypentyl)amino]phenol, and 4-bis[(6-hydroxyhexyl)amino]phenol.

16. The method of claim 1 wherein the-unsaturated cyclic aliphatic compound is selected from the group consisting of cyclopentadiene, dicyclopentadiene, and indene.

17. The method of claim 1 wherein the polymerizable monomer is selected from the group consisting of alkylated styrene, chloroprene, α-methylstyrene, styrene, styrene sulfonic acid, vinyltoluene, and divinylbenzene.

18. The method of claim 1, wherein the method is for inhibiting polymerization of monomers in a hydrocarbon-containing and monomer-containing processing stream, and wherein the composition comprises a processing stream that includes one or more non-polymerizable hydrocarbons and the monomer, the processing stream optionally comprising a petroleum process stream.

19. The method of claim 18 wherein the processing stream has a temperature in the range of 100 ° C. to 400 ° C., and the nitrogen- and oxygen-containing aromatic antipolymerant is stable and has antipolymerant activity in the processing stream.

20. The method of claim 18, wherein the one or more non-polymerizable hydrocarbons and the monomer are from crude oil, reduced crude oil, crude distillate, heavy oil, bitumen, hydrotreated oil, refined oil, or pyrolysis oil.

21. The method of claim 1, wherein the nitrogen- and oxygen-containing aromatic antipolymerant is present in the composition in an amount in the range of 10 to 50000 ppm, in an amount in the range of 50 to 5000 ppm, or in an amount in the range of 100 to 300 ppm.

22. The method of claim 1 wherein the composition has no, less than 5 ppm, or less than 0.5 ppm of a nitroxyl group containing antipolymerant, wherein the nitroxyl group containing antipolymerant is optionally a nitroxide-containing compound selected from the group consisting of 2,2,6,6-tetramethylpiperidinyl-1-oxyl (TEMPO), 4-hydroxy-2,2,6, 6-tetramethylpiperidinyl-1-oxyl(HTMPO), and 4-oxo-2,2,6, 6-tetramethylpiperidinyl-1-oxyl(OTEMPO).

* * * * *